US007582458B2

(12) United States Patent
Grichko

(10) Patent No.: US 7,582,458 B2
(45) Date of Patent: Sep. 1, 2009

(54) FERMENTATION PROCESSES AND COMPOSITIONS

(75) Inventor: Varvara Grichko, Raleigh, NC (US)

(73) Assignee: Novozymes North America, Inc., Franklinton, NC (US)

( * ) Notice: Subject to any disclaimer, the term of this patent is extended or adjusted under 35 U.S.C. 154(b) by 300 days.

(21) Appl. No.: 11/299,163

(22) Filed: Dec. 9, 2005

(65) Prior Publication Data

US 2007/0134780 A1    Jun. 14, 2007

Related U.S. Application Data

(63) Continuation of application No. PCT/US2004/018342, filed on Jun. 9, 2004, which is a continuation of application No. 10/459,315, filed on Jun. 10, 2003, now abandoned.

(51) Int. Cl.
*C12P 9/02* (2006.01)
*C12P 7/06* (2006.01)

(52) U.S. Cl. ............... 435/161; 435/165; 435/189; 435/254.2

(58) Field of Classification Search ............ None
See application file for complete search history.

(56) References Cited

U.S. PATENT DOCUMENTS

| 4,288,550 | A | | 9/1981 | Ishida et al. |
| 4,490,469 | A | * | 12/1984 | Kirby et al. .............. 435/161 |
| 4,642,236 | A | | 2/1987 | Friend et al. |
| 5,100,791 | A | * | 3/1992 | Spindler et al. .......... 435/163 |
| 5,464,761 | A | | 11/1995 | Muller et al. |
| 5,733,473 | A | | 3/1998 | Johnston et al. |
| 2007/0141688 | A1 | * | 6/2007 | Henderson et al. ........ 435/161 |
| 2007/0190627 | A1 | * | 8/2007 | Henderson et al. ........ 435/161 |

FOREIGN PATENT DOCUMENTS

| WO | WO 02/20730 | 3/2002 |
| WO | WO 02/086114 | 10/2002 |
| WO | WO/02/086114 | 10/2002 |

OTHER PUBLICATIONS

De Buck et al, "Taints, Off Flavors & Malodors Bibliopgraphy: Lipoxygenase effects in beer staling" Cerevisia 1998 vol. 23, No. 2 Abstract pp. 25-37.*
Vandamme et al., Journal of Chemical Technology and Biotechnology, vol. 77, pp. 1323-1332 (2002).
Shiba et al., Cereal Chemistry, vol. 67, No. 4, pp. 350-355 (1990).

* cited by examiner

*Primary Examiner*—Herbert J. Lilling
(74) *Attorney, Agent, or Firm*—Elias J. Lambiris; Jennifer L. Fox

(57) ABSTRACT

The present invention provides improved fermentation processes, including for use in an ethanol production process. The improved fermentation processes include applying at least one fatty acid oxidizing enzyme (especially a lipoxygenase) in a fermentation process. The improved fermentation process may also involve the addition of various additional enzymes and growth stimulators for the fermenting microorganisms, including vitamins and mineral.

14 Claims, No Drawings

FERMENTATION PROCESSES AND COMPOSITIONS

CROSS-REFERENCE TO RELATED APPLICATIONS

This application is a continuation of PCT/US2004/018342 filed Jun. 9, 2004, which is a continuation of U.S. application Ser. No. 10/459,315 filed Jun. 10, 2003, now abandoned the contents of which are fully incorporated herein by reference.

FIELD OF THE INVENTION

The present invention relates to enzymatic processes and compositions for producing fermentation products, including processes and compositions for improving yeast performance during fermentation processes.

BACKGROUND OF THE INVENTION

Fermentation processes are used for making a vast number of commercial products, including alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in the consumable alcohol industry (e.g., beer and wine), dairy industry (e.g., in the production of yogurt and cheese), leather industry, and tobacco industry.

There is a need for further improvement of fermentation processes and for improved processes which include a fermentation step.

SUMMARY OF THE INVENTION

The present invention provides processes and compositions for producing fermentation products. The present invention also provides improved processes for producing ethanol using one or more of the processes described herein. According to the invention the percentage of (recycled) backset, as will be defined further below, in the fermentation medium may be increased significantly leading to a reduced need for feeding additional water to the fermentation process. Further, the more efficient utilization of the fermentation material reduces the cost of the fermentation process, because more starch-containing starting material is converted into fermentation product, such as ethanol, and carbohydrate nutrition for the fermenting organism(s).

In the first aspect the invention relates to a process for producing a fermentation product in a fermentation medium, which process comprises a fermentation step, comprising subjecting the fermentation medium to at least one fatty acid oxidizing enzyme.

In one embodiment of the present invention at least one fatty acid oxidizing enzyme is applied to the fermentation medium before or during fermentation. In a preferred embodiment, the invention comprises contacting the fermentation medium with at least one fatty acid oxidizing enzyme. The fatty acid oxidizing enzyme may in one embodiment be used to pre-treat the backset before recycling it to the fermenter/fermentation container. In another embodiment the fatty acid oxidizing enzyme treatment is performed directly on the fermentation media with or without the backset portion. In a preferred embodiment the fatty acid oxidizing enzyme is added directly to the fermentation medium comprising recycled backset. In an embodiment the fatty acid oxidizing enzyme is added before or during fermentation process. The fatty acid oxidizing enzyme may be added to the fermentation medium before the addition of fermenting organism(s), such as yeast, but may also be added together with or after addition of the fermenting organism(s). It is preferred to add the fatty acid oxidizing enzyme before the initiation of the fermentation. However, it is also within the scope of the invention to add the fatty acid oxidizing enzyme during fermentation, such as after initiation of the fermentation. In a preferred embodiment the fermentation medium comprising a backset portion is pre-treated with a fatty acid oxidizing enzyme.

The fatty acid oxidizing enzyme may be applied in an effective amount before and/or during fermentation. The fatty acid oxidizing enzyme may be applied in an effective amount before fermentation, such as, during propagation of the fermenting microorganism(s) or after propagation of the fermenting microorganism(s).

In a preferred embodiment of the present invention the fatty acid oxidizing enzyme is a lipoxygenase. In a preferred embodiment the fermenting microorganism is yeast.

In an embodiment, the fermentation process of the present invention is used in combination with a saccharification step (SSF) or both a liquefaction step and a saccharification step (LSF). In addition to at least one fatty acid oxidizing enzyme other enzymatic activities may be added. Such enzyme activities include esterase activity, preferably lipase and/or cutinase activity, laccase activity, phytase activity, cellulase activity, xylanase activity, alpha-amylase activity or glucoamylase activity.

In a preferred embodiment, the fermentation process is used for producing an alcohol, preferably ethanol. The presence of at least one fatty acid oxidizing enzyme may be used to raise the ethanol yield. By using at least one fatty acid oxidizing enzyme in accordance with the invention it is possible to increase the percentage of (recycled) backset in the fermentation medium. The backset may constitute up to 30% w/w, preferably up to 50% w/w, more preferably 70% w/w, and even up to more than 90% w/w of the liquid portion (i.e., backset and water portions) of the fermentation medium before initiation of the fermentation. In other words, this means that for instance recycling of 50% w/w backset corresponds to a fermentation medium (slurry) comprising 36% w/w (ground) grain material, 32% w/w water and 32% w/w backset.

The term "backset" refers to the liquid portion obtained from the co-product (i.e. whole stillage) coming from the fermentation step—after dividing (separating) the fermentation co-product (i.e., whole stillage) into a solid portion (i.e., wet grains) and a liquid "backset" portion. The "backset" portion is sometimes referred to as "thin stillage". Backset comprises about 10% solids and usually contains various compounds that are inhibitory to the fermentation process and thus may lead to a decreased ethanol yield. Therefore, the addition of backset is in general avoided.

According to the invention this problem may be overcome by subjecting the fermentation medium to at least one fatty acid oxidizing enzyme. In a preferred embodiment the fermentation is performed in the presence of one or more additional enzyme activities. The additional enzyme(s) may be introduced prior to, during/simultaneous with or after the fatty acid oxidizing enzyme. The fatty acid oxidizing enzyme may be used in combination with one or more of the following enzymes: esterase, such as lipase and/or cutinase, phytase, laccase, protease, cellulase, xylanase, amylase and/or glucoamylase, of mixtures thereof.

In another embodiment of the present invention stimulator(s) for growth of the fermenting microorganism(s) is(are) added/present in combination with the fatty acid oxidizing enzyme and optionally an additional enzymatic activity described herein, to further improve the fermentation process. Preferred stimulators for growth include vitamins and minerals.

In a final aspect the invention relates to a composition comprising a fatty acid oxidizing enzyme and an additional enzyme and/or a stimulator.

DETAILED DESCRIPTION OF THE INVENTION

The present invention provides processes and compositions for producing a fermentation product in which at least one fatty acid oxidizing enzyme is used in the fermentation process.

Treatment of the fermentation medium with a fatty acid oxidizing enzyme prior to or during fermentation increases the fermentation yield. Further, treatment of the fermentation medium, which includes a portion of backset, with a fatty acid oxidizing enzyme increases the fermentation yield compared to the yield obtained without addition of the fatty acid oxidizing enzyme. The addition of one or more additional enzyme activities results in further fermentation yield improvements.

Although not limited to any one theory of operation, the use of a fatty acid oxidizing enzyme in the fermentation processes according to the present invention is believed to be based on the increased starch release, due to disruption of amyloplast membranes, from the grain material. Also, the fatty acid oxidizing enzyme promotes the formation of S-S bridges in proteins. This is believed to increase the slurry stability.

In the first aspect the invention relates to a process for producing a fermentation product in a fermentation medium, which process comprises a fermentation step, comprising subjecting the fermentation medium to at least one fatty acid oxidizing enzyme.

The fatty acid oxidizing enzyme treatment may be applied at any stage in the fermentation process. In a preferred embodiment, the fatty acid oxidizing enzyme is added, in an effective amount, during fermentation (e.g., by contacting the fermentation medium), such as, at the start of the fermentation process. In another preferred embodiment, the fatty acid oxidizing enzyme is added in an effective amount prior to fermentation, such as, during propagation of the fermenting organism(s) or after propagation or during a saccharification or a pre-saccharification step or liquefaction step. The fermentation process of the invention may be used for producing alcohol, such as ethanol, e.g., as an integral part of a traditional ethanol process.

Fermentation Process

"Fermentation" or "fermentation process" refers to any fermentation process or any process comprising a fermentation step. A fermentation process of the invention includes, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. Fermentation processes also include fermentation processes used in the consumable alcohol industry (e.g., beer and wine), dairy industry (e.g., fermented dairy products), leather industry and tobacco industry. Preferred fermentation processes include alcohol fermentation processes, which are well known in the art. Preferred fermentation processes are anaerobic fermentation processes, which are well known in the art.

In a preferred embodiment, the fermentation process of the present invention is used in combination with a liquefaction process and/or saccharification process, in which additional enzymatic activities, such as esterase, including lipase and/or cutinase; phytase; laccase; cellulase; xylanase; alpha-amylase; glucoamylase; or mixtures thereof, may be used for processing the substrate, e.g., a starch substrate.

In yet another preferred embodiment, the fermentation process of the invention is used in a process of producing ethanol. In a preferred embodiment of the invention the fatty acid oxidizing enzyme is lipoxygenase.

Fermentation Media

"Fermentation media" or "fermentation medium" refers to the environment in which the fermentation is carried out and which includes the fermentation substrate, that is, the carbohydrate source that is metabolized by the fermenting microorganism(s). The fermentation media, including fermentation substrate and other raw materials used in the fermentation process of the invention may be processed, e.g., by milling, liquefaction and/or saccharification or other desired process step(s) prior to or simultaneously with the fermentation process. Accordingly, the fermentation medium can refer to the medium before the fermenting microorganism(s) is(are) added, such as, the medium in or resulting from a liquefaction and/or saccharification process, as well as the media which comprises the fermenting microorganism(s), such as, the media used in a simultaneous saccharification and fermentation process (SSF) or simultaneous liquefaction-saccharification-fermentation (LSF) process.

Fermenting Organism

"Fermenting microorganism" refers to any microorganism suitable for use in a desired fermentation process. Suitable fermenting microorganisms according to the invention are able to ferment, i.e., convert, sugars, such as glucose and/or maltose, directly or indirectly into the desired fermentation product. Examples of fermenting microorganisms include fungal organisms, such as yeast. Preferred yeast includes strains of *Sacchromyces* spp., and in particular, *Sacchromyces cerevisiae*. Commercially available yeast include, e.g., Red Star®/Lesaffre Ethanol Red (available from Red Star/Lesaffre, USA), SUPERSTART (available from Alltech), GERT STRAND (available from Gert Strand AB, Sweden) and FERMIOL (available from DSM Specialties).

Fermentation Substrate

Any suitable substrate or raw material may be used in a fermentation process of the present invention. The substrate is generally selected based on the desired fermentation product and the process employed, as is well known in the art. Examples of substrates suitable for use in the processes of present invention, include starch-containing materials, such as tubers, roots, whole grains, corns, cobs, wheat, barley, rye, milo or cereals, sugar-containing raw materials, such as molasses, fruit materials, sugar, cane or sugar beet, potatoes, and cellulose-containing materials, such as wood or plant residues. Suitable substrates also include carbohydrate sources, in particular, low molecular sugars ($DP_{1-3}$ sugars) that can be metabolized by the fermenting microorganism(s), and which may be supplied by direct addition to the fermentation media.

Fatty Acid Oxidizing Enzyme

The term "a" fatty acid oxidizing enzyme means at least one of such enzymes. The term "at least one" means one, two, three, four, five, six or even more of such enzymes.

In the present context, a "fatty acid oxidizing enzyme" is an enzyme which hydrolyzes the substrate linoleic acid more efficiently than the substrate syringaldazine. "More efficiently" means with a higher reaction rate. This can be tested using the method described in Example 2, and calculating the difference between (1) absorbancy increase per minute on the substrate linoleic acid (absorbancy at 234 nm), and (2) absorbancy increase per minute on the substrate syringaldazine (absorbancy at 530 nm), i.e. by calculating the Reaction Rate Difference (RRD) $=(d(A_{234})/dt - d(A_{530})/dt)$. If the RRD is above zero, the enzyme in question qualifies as a fatty acid oxidizing enzyme as defined herein. If the RRD is zero, or below zero the enzyme in question is not a fatty acid oxidizing enzyme.

In particular embodiments, the RRD is at least 0.05, 0.10, 0.15, 0.20, or at least 0.25 absorbancy units/minute.

In a particular embodiment of the method of Example 2, the enzymes are well-defined. Still further, for the method of Example 2 the enzyme dosage is adjusted so as to obtain a maximum absorbancy increase per minute at 234 nm, or at 530 nm. In particular embodiments, the maximum absorbancy increase is within the range of 0.05-0.50; 0.07-0.4; 0.08-0.3; 0.09-0.2; or 0.10-0.25 absorbancy units pr. min. The enzyme dosage may for example be in the range of 0.01-20; 0.05-15; or 0.10-10 mg enzyme protein per ml.

In the alternative, a "fatty acid oxidizing enzyme" may be defined as an enzyme capable of oxidizing unsaturated fatty acids more efficiently than syringaldazine. The activity of the enzyme could be compared in a standard oximeter setup as described in Example 1 of the present application at pH 6 and 30° C. including either syringaldazine or linoleic acid as substrates.

In a particular embodiment, the fatty acid oxidizing enzyme is defined as an enzyme classified as EC 1.11.1.3, or as EC 1.13.11.-. EC 1.13.11.- means any of the sub-classes thereof, presently forty-nine: EC 1.13.11.1-EC 1.13.11.49. EC 1.11.1.3 is designated fatty acid peroxidase, and EC 1.13.11.- is designated oxygenases acting on single donors with incorporation of two atoms of oxygen.

In a further particular embodiment, the EC 1.13.11.- enzyme is classified as EC 1.13.11.12, EC 1.13.11.31, EC 1.13.11.33, EC 1.13.11.34, EC 1.13.11.40, EC 1.13.11.44 or EC 1.13.11.45, designated lipoxygenase, arachidonate 12-lipoxygenase, arachidonate 15-lipoxygenase, arachidonate 5-lipoxygenase, arachidonate 8-lipoxygenase, linoleate diol synthase, and linoleate 11-lipoxygenase, respectively).

Examples of effective amounts of fatty acid oxidizing enzyme are from 0.001 to 400 U/g DS (Dry Solids). Preferably, the fatty acid oxidizing enzyme is used in an amount of 0.01 to 100 U/g DS, more preferably 0.05 to 50 U/g DS, and even more preferably 0.1 to 20 U/g DS. Further optimization of the amount of fatty acid oxidizing enzyme can hereafter be obtained using standard procedures known in the art.

Lipoxygenase

In a preferred embodiment, the fatty acid oxidizing enzyme is a lipoxygenase (LOX), classified as EC 1.13.11.12, which is an enzyme that catalyzes the oxygenation of polyunsaturated fatty acids, especially cis,cis-1,4-dienes, e.g., linoleic acid and produces a hydroperoxide. But also other substrates may be oxidized, e.g., monounsaturated fatty acids.

Microbial lipoxygenases can be derived from, e.g., *Saccharomyces cerevisiae*, *Thermoactinomyces vulgaris*, *Fusarium oxysporum*, *Fusarium proliferatum*, *Thermomyces lanuginosus*, *Pyricularia oryzae*, and strains of *Geotrichum*. The preparation of a lipoxygenase derived from *Gaeumannomyces graminis* is described in Examples 3-4 of WO 02/20730. The expression in *Aspergillus oryzae* of a lipoxygenase derived from *Magnaporthe salvinii* is described in Example 2 of WO 02/086114, and this enzyme can be purified using standard methods, e.g. as described in Example 4 of WO 02/20730.

Lipoxygenase (LOX) may also be extracted from plant seeds, such as soybean, pea, chickpea, and kidney bean. Alternatively, lipoxygenase may be obtained from mammalian cells, e.g. rabbit reticulocytes.

Lipoxygenase activity may be determined as described in the "Materials and Methods" section below.

An example of an effective amount of lipoxygenase (LOX) is from 0.001 to 400 U/g DS (Dry Solids). Preferably, the lipoxygenase is used in an amount of 0.01 to 100 U/g DS, more preferably 0.05 to 50 U/g DS, and even more preferably 0.1 to 20 U/g DS. Further optimization of the amount of lipoxygenase can hereafter be obtained using standard procedures known in the art.

Additional Enzymes

In a preferred embodiment of the invention one or more additional enzyme activities may be used in combination with (such as prior to, during or following) the fatty acid oxidizing enzyme treatment of the present invention. Preferred additional enzymes are esterases, such as lipases and/or cutinases, phytase, laccase, proteases, cellulases, xylanases, amylases, such as alpha-amylases, maltogenic alpha-amylases, beta-amylases, or glucoamylases, or mixtures thereof.

In another preferred embodiment of the present invention stimulators for growth of the fermenting microorganism is(are) added in combination with the enzymatic activities described herein, to further improve the fermentation process. Preferred stimulators for growth include vitamins and minerals.

Esterases

In a preferred embodiment of the invention the fatty acid oxidizing enzyme is applied in an effective amount prior to or during fermentation in combinations with an effective amount of esterase. The enzymes may be added prior to or during fermentation, including during or after the propagation of the fermenting microorganisms. The enzymes may also be used to pre-treat the fermentation medium (e.g., with or without addition of backset).

As used herein, an "esterase" also referred to as a carboxylic ester hydrolyases, refers to enzymes acting on ester bonds, and includes enzymes classified in EC 3.1.1 Carboxylic Ester Hydrolases according to Enzyme Nomenclature (available at http://www.chem.qmw.ac.uk/iubmb/enzyme or from Enzyme Nomenclature 1992, Academic Press, San Diego, Calif., with Supplement 1 (1993), Supplement 2 (1994), Supplement 3 (1995), Supplement 4 (1997) and Supplement 5, in Eur. J. Biochem. 1994, 223, 1-5; Eur. J. Biochem. 1995, 232, 1-6; Eur. J. Biochem. 1996, 237, 1-5; Eur. J. Biochem. 1997, 250; 1-6, and Eur. J. Biochem. 1999, 264, 610-650; respectively). Non-limiting examples of esterases include arylesterase, triacylglycerol lipase, acetylesterase, acetylcholinesterase, cholinesterase, tropinesterase. pectinesterase, sterol esterase, chlorophyllase, L-arabinonolactonase, gluconolactonase, uronolactonase, tannase, retinyl-palmitate esterase, hydroxybutyrate-dimer hydrolase, acylglycerol lipase, 3-oxoadipate enol-lactonase, 1,4-lactonase, galactolipase, 4-pyridoxolactonase, acylcarnitine hydrolase, aminoacyl-tRNA hydrolase, D-arabinonolactonase, 6-phosphogluconolactonase, phospholipase A1, 6-acetylglucose deacetylase, lipoprotein lipase, dihydrocoumarin lipase, limonin-D-ring-lactonase, steroid-lactonase, triacetate-lactonase, actinomycin lactonase, orsellinate-depside hydrolase, cephalosporin-C deacetylase, chlorogenate hydrolase, alpha-amino-acid esterase, 4-methyloxaloacetate esterase, carboxymethylenebutenolidase, deoxylimonate A-ring-lactonase, 2-acetyl-1-alkylglycerophosphocholine esterase, fusarinine-C ornithinesterase, sinapine esterase, wax-ester hydrolase, phorbol-diester hydrolase, phosphatidylinositol deacylase, sialate 0-acetylesterase, acetoxybutynyl-bithiophene deacetylase, acetylsalicylate deacetylase, methylumbelliferyl-acetate deacetylase, 2-pyrone-4,6-dicarboxylate lactonase, N-acetylgalactosaminoglycan deacetylase, juvenile-hormone esterase, bis(2-ethylhexyl)phthalate esterase, protein-glutamate methylesterase, 11-cis-retinyl-palmitate hydrolase, all-trans-retinyl-palmitate hydrolase, L-rhamnono-1,4-lactonase, 5-(3,4-diacetoxybut-1-ynyl)-2, 2'-bithiophene deacetylase, fatty-acyl-ethyl-ester synthase, xylono-1,4-lactonase, N-acetylglucosaminylphosphatidylinositol deacetylase, cetraxate benzylesterase, acetylalkylglycerol acetylhydrolase, and acetylxylan esterase.

Preferred esterases according to the present invention are lipolytic enzymes, such as, lipases (as classified by EC 3.1.1.3, EC 3.1.1.23 and/or EC 3.1.1.26) and phospholipases (as classified by EC 3.1.1.4 and/or EC 3.1.1.32, including lysophospholipases as classified by EC 3.1.1.5). Other preferred esterases are cutinases (as classified by EC 3.1.1.74).

When used in combination with processes or treatments which employ other enzymes, beside the fatty acid oxidizing enzyme, such as, phytase, laccase, amylase and glucoamylase which are used in, e.g., liquefaction and/or saccharification processes, an esterase composition which does not inhibit these other enzymes are preferred. For instance, e.g., esterases which do not contain or contain only minor amounts of calcium-binding compounds are preferred. Similarly, esterases which do not inhibit the fermentation process are preferred. For instance, esterases which do not contain or which contain only minor amounts of glycerol are preferred.

The esterase may be added in an amount effective to obtain the desired benefit to improve the performance of the fermenting microorganism(s), e.g., to change the lipid composition/concentration inside and/or outside of the fermenting microorganism(s) or in the cell membrane of the fermenting microorganism(s), to result in an improvement in the movement of solutes into and/or out of the fermenting microorganism(s) during fermentation and/or to provide more metabolizable energy sources (such as, e.g., by converting components, such as, oil from the corn substrate, to components useful the fermenting microorganism(s), e.g., unsaturated fatty acids and glycerol), to increase ethanol yield. Examples of effective amounts of esterase are from 0.01 to 400 LU/g DS (Dry Solids). Preferably, the esterase is used in an amount of 0.1 to 100 LU/g DS, more preferably 0.5 to 50 LU/g DS, and even more preferably 1 to 20 LU/g DS. Further optimization of the amount of esterase can hereafter be obtained using standard procedures known in the art.

In a preferred embodiment the esterase is a lipolytic enzyme, more preferably, a lipase. As used herein, a "lipolytic enzymes" refers to lipases and phospholipases (including lysophospholipases). The lipolytic enzyme is preferably of microbial origin, in particular of bacterial, fungal or yeast origin. The lipolytic enzyme used may be derived from any source, including, for example, a strain of *Absidia*, in particular *Absidia blakesleena* and *Absidia corymbifera*, a strain of *Achromobacter*, in particular *Achromobacter iophagus*, a strain of *Aeromonas*, a strain of *Alternaria*, in particular *Altemaria brassiciola*, a strain of *Aspergillus*, in particular *Aspergillus niger* and *Aspergillus flavus*, a strain of *Achromobacter*, in particular *Achromobacter iophagus*, a strain of *Aureobasidium*, in particular *Aureobasidium pullulans*, a strain of *Bacillus*, in particular *Bacillus pumilus*, *Bacillus strearothermophilus* and *Bacillus subtilis*, a strain of *Beauveria*, a strain of *Brochothrix*, in particular *Brochothrix thermosohata*, a strain of *Candida*, in particular *Candida cylindracea* (*Candida rugosa*), *Candida paralipolytica*, and *Candida antarctica*, a strain of *Chromobacter*, in particular *Chromobacter viscosum*, a strain of *Coprinus*, in particular *Coprinus cinerius*, a strain of *Fusarium*, in particular *Fusarium oxysporum*, *Fusarium solani*, *Fusarium solani pisi*, and *Fusarium roseum culmorum*, a strain of *Geotricum*, in particular *Geotricum penicillatum*, a strain of *Hansenula*, in particular *Hansenula anomala*, a strain of *Humicola*, in particular *Humicola brevispora*, *Humicola brevis* var. *thermoidea*, and *Humicola insolens*, a strain of *Hyphozyma*, a strain of *Lactobacillus*, in particular *Lactobacillus curvatus*, a strain of *Metarhizium*, a strain of *Mucor*, a strain of *Paecilomyces*, a strain of *Penicillium*, in particular *Penicillium cyclopium*, *Penicillium crustosum* and *Penicillium expansum*, a strain of *Pseudomonas* in particular *Pseudomonas aeruginosa*, *Pseudomonas alcaligenes*, *Pseudomonas cepacia* (syn. *Burkholderia cepacia*), *Pseudomonas fluorescens*, *Pseudomonas fragi*, *Pseudomonas maltophilia*, *Pseudomonas mendocina*, *Pseudomonas mephitica lipolytica*, *Pseudomonas alcaligenes*, *Pseudomonas plantari*, *Pseudomonas pseudoalcaligenes*, *Pseudomonas putida*, *Pseudomonas stutzeri*, and *Pseudomonas wisconsinensis*, a strain of *Rhizoctonia*, in particular *Rhizoctonia solani*, a strain of *Rhizomucor*, in particular *Rhizomucor miehei*, a strain of *Rhizopus*, in particular *Rhizopus japonicus*, *Rhizopus microsporus* and *Rhizopus nodosus*, a strain of *Rhodosporidium*, in particular *Rhodosporidium toruloides*, a strain of *Rhodotorula*, in particular *Rhodotorula glutinis*, a strain of *Sporobolomyces*, in particular *Sporobolomyces shibatanus*, a strain of *Thernomyces*, in particular *Thermomyces lanuginosus* (formerly *Humicola lanuginosa*), a strain of *Thiarosporella*, in particular *Thiarosporella phaseolina*, a strain of *Trichoderma*, in particular *Trichoderma harzianum*, and *Trichoderma reesei*, and/or a strain of *Verticillium*.

In a preferred embodiment, the lipolytic enzyme is derived from a strain of *Aspergillus*, a strain of *Achromobacter*, a strain of *Bacillus*, a strain of *Candida*, a strain of *Chromobacter*, a strain of *Fusarium*, a strain of *Humicola*, a strain of *Hyphozyma*, a strain of *Pseudomonas*, a strain of *Rhizomucor*, a strain of *Rhizopus*, or a strain of *Thermomyces*.

In more preferred embodiments, the lipolytic enzyme is a lipase. Lipases may be applied herein for their ability to modify the structure and composition of triglyceride oils and fats in the fermentation media (including fermentation yeast), for example, resulting from a corn substrate. Lipases catalyze different types of triglyceride conversions, such as hydrolysis, esterification and transesterification. Suitable lipases include acidic, neutral and basic lipases, as are well-known in the art, although acidic lipases (such as, e.g., the lipase G AMANO 50, available from Amano) appear to be more effective at lower concentrations of lipase as compared to either neutral or basic lipases. Preferred lipases for use in the present invention included *Candida antarcitca* lipase and *Candida cylindracea* lipase. More preferred lipases are purified lipases such as *Candida antarcitca* lipase (lipase A), *Candida antarcitca* lipase (lipase B), *Candida cylindracea* lipase, and *Penicillium camembertii* lipase.

The lipase the one disclosed in EP 258,068-A or may be a lipase variant such as a variant disclosed in WO 00/60063 or WO 00/32758, which is hereby incorporated by reference. Preferred commercial lipases include LECITASE™, LIPO-LASE™ and LIPEX™ (available from Novozymes A/S, Denmark) and G AMANO 50 (available from Amano).

Lipases are preferably added in amounts from about 1 to 400 LU/g DS, preferably 1 to 10 LU/g DS, and more preferably 1 to 5 LU/g DS.

In another preferred embodiment of the present invention, the at least one esterase is a cutinase. Cutinases are enzymes which are able to degrade cutin. The cutinase may be derived from any source. In a preferred embodiment, the cutinase is derived from a strain of *Aspergillus*, in particular *Aspergillus oryzae*, a strain of *Alternaria*, in particular *Alternaria brassiciola*, a strain of *Fusarium*, in particular *Fusarium solani*, *Fusarium solani pisi*, *Fusarium roseum culmorum*, or *Fusarium roseum sambucium*, a strain of *Helminthosporum*, in particular *Helminthosporum sativum*, a strain of *Humicola*, in particular *Humicola insolens*, a strain of *Pseudomonas*, in particular *Pseudomonas mendocina*, or *Pseudomonas putida*, a strain of *Rhizoctonia*, in particular *Rhizoctonia solani*, a strain of *Streptomyces*, in particular *Streptomyces scabies*, or a strain of *Ulocladium*, in particular *Ulocladium consortiale*. In a most preferred embodiment the cutinase is derived from a strain of *Humicola insolens*, in particular the strain *Humicola insolens* DSM 1800. *Humicola insolens* cutinase is described in WO 96/13580 which is herby incorporated by reference. The cutinase may be a variant, such as one of the variants disclosed in WO 00/34450 and WO 01/92502, which are hereby incorporated by reference. Preferred cutinase variants include variants listed in Example 2 of WO 01/92502, which is hereby specifically incorporated by reference. An effective amount of cutinase is between 0.01 and 400 LU/g DS, preferably from about 0.1 to 100 LU/g DS, more preferably, 1 to 50 LU/g DS. Further optimization of the amount of cutinase can hereafter be obtained using standard procedures known in the art.

In another preferred embodiment, the at least one esterase is a phospholipase. As used herein, the term phospholipase is an enzyme which has activity towards phospholipids. Phospholipids, such as lecithin or phosphatidylcholine, consist of glycerol esterified with two fatty acids in an outer (sn-1) and the middle (sn-2) positions and esterified with phosphoric acid in the third position; the phosphoric acid, in turn, may be esterified to an amino-alcohol. Phospholipases are enzymes which participate in the hydrolysis of phospholipids. Several types of phospholipase activity can be distinguished, including phospholipases $A_1$ and $A_2$ which hydrolyze one fatty acyl group (in the sn-1 and sn-2 position, respectively) to form lysophospholipid; and lysophospholipase (or phospholipase B) which can hydrolyze the remaining fatty acyl group in lysophospholipid. Phospholipase C and phospholipase D (phosphodiesterases) release diacyl glycerol or phosphatidic acid respectively.

The term phospholipase includes enzymes with phospholipase activity, e.g., phospholipase A ($A_1$ or $A_2$), phospholipase B activity, phospholipase C activity or phospholipase D activity. The term "phospholipase A" used herein in connection with an enzyme of the invention is intended to cover an enzyme with Phospholipase $A_1$ and/or Phospholipase $A_2$ activity. The phospholipase activity may be provided by enzymes having other activities as well, such as, e.g., a lipase with phospholipase activity. The phospholipase activity may, e.g., be from a lipase with phospholipase side activity. In other embodiments of the invention the phospholipase enzyme activity is provided by an enzyme having essentially only phospholipase activity and wherein the phospholipase enzyme activity is not a side activity.

The phospholipase may be of any origin, e.g;, of animal origin (such as, e.g., mammalian), e.g. from pancreas (e.g. bovine or porcine pancreas), or snake venom or bee venom. Alternatively, the phospholipase may be of microbial origin, e.g. from filamentous fungi, yeast or bacteria, such as the genus or species *Aspergillus*, e.g., *A. niger*, *Dictyostelium*, e.g. *D. discoideum; Mucor*, e.g. *M. javanicus, M. mucedo, M. subtilissimus; Neurospora*, e.g. *N. crassa; Rhizomucor*, e.g., *R. pusillus; Rhizopus*, e.g. *R. arrhizus, R. japonicus, R. stolonifer; Sclerotinia*, e.g., *S. libertiana; Trichophyton*, e.g. *T. rubrum; Whetzelinia*, e.g. *W. sclerotiorum; Bacillus*, e.g., *B. megaterium, B. subtilis; Citrobacter*, e.g., *C. freundii; Enterobacter*, e.g., *E. aerogenes, E. cloacae Edwardsiella, E. tarda; Erwinia*, e.g., *E. herbicola; Escherichia*, e.g., *E. coli; Klebsiella*, e.g., *K. pneumoniae; Proteus*, e.g., *P. vulgaris; Providencia*, e.g. *P. stuartii; Salmonella*, e.g. *S. typhimurium; Serratia*, e.g., *S. liquefasciens, S. marcescens; Shigella*, e.g., *S. flexneri; Streptomyces*, e.g., *S. violeceoruber; Yersinia*, e.g., *Y. enterocolitica*. Thus, the phospholipase may be fungal, e.g., from the class Pyrenomycetes, such as the genus *Fusarium*, such as a strain of *F. culmorum, F. heterosporum, F. solani*, or a strain of *F. oxysporum*. The phospholipase may also be from a filamentous fungus strain within the genus *Aspergillus*, such as a strain of *Aspergillus awamori, Aspergillus foetidus, Aspergillus japonicus, Aspergillus niger* or *Aspergillus oryzae*. Preferred commercial phospholipases include LECITASE™ and LECITASE™ ULTRA (available from Novozymes A/S, Denmark).

An effective amount of phosphorlipase is between 0.01 and 400 LU/g DS, preferably from about 0.1 to 100 LU/g DS, more preferably, 1 to 50 LU/g DS. Further optimization of the amount of phosphorlipase can hereafter be obtained using standard procedures known in the art.

Phytase

In a preferred embodiment the fatty acid oxidizing enzyme is used in combination with an effcient amount of phytase. In accordance with this embodiment, a phytase may be used to promote the liberation of inorganic phosphate from phytic acid (myo-inositol hexakisphosphate) or from any salt thereof (phytates) present in the medium.

Phytases can be classified according to their specificity in the initial hydrolysis step, viz. according to which phosphate-ester group is hydrolyzed first. The phytase to be used may have any specificity, e.g., a 3-phytase (E.C. 3.1.3.8), a 6-phytase (E.C. 3.1.3.26) or a 5-phytase (no E.C. number).

The phytase may be added during the fermentation or prior to fermentation, such as, during propogation or in a step prior to fermentation, e.g., a liquefaction and/or saccharification step. The phytases may be added, e.g., to improve the bioavailability of essential minerals to yeast, as described in WO 01/62947, which is hereby incorporated by reference. The phytase may also be used to pre-treat the fermentation medium (e.g., with or without backset).

The phytase may be derived from plants or microorganisms, such as bacteria or fungi, e.g., yeast or filamentous fungi. The plant phytase may be from wheat-bran, maize, soy bean or lily pollen. Suitable plant phytases are described in Thomlinson et al, Biochemistry, 1 (1962), 166-171; Barrientos et al, Plant. Physiol., 106 (1994), 1489-1495; WO 98/05785; WO 98/20139.

A bacterial phytase may be from the genera *Bacillus*, *Pseudomonas* or *Escherichia*, preferably the species *B. subtilis* or *E. coli*. Suitable bacterial phytases are described in Paver and Jagannathan, 1982, Journal of Bacteriology 151: 1102-1108; Cosgrove, 1970, Australian Journal of Biological Sciences 23:1207-1220; Greiner et al, Arch. Biochem. Biophys., 303, 107-113, 1993; WO 98/06856; WO 97/33976; WO 97/48812.

A yeast phytase or myo-inositol monophosphatase may be derived from genus *Saccharomyces* or *Schwanniomyces*, preferably species *Saccharomyces cerevisiae* or *Schwanniomyces occidentalis*. Suitable yeast phytases are described in Nayini et al, 1984, Lebensmittel Wissenschaft und Technologie 17:24-26; Wodzinski et al, Adv. Appl. Microbiol., 42, 263-303; AU-A-24840/95;

Phytases from filamentous fungi may be derived from the fungal phylum of *Ascomycota* (ascomycetes) or the phylum Basidiomycota, e.g., the genus *Aspergillus*, *Thermomyces* (also called *Humicola*), *Myceliophthora*, *Manascus*, *Penicillium*, *Peniophora*, *Agrocybe*, *Paxillus*, or *Trametes*, preferably the species *Aspergillus terreus*, *Aspergillus niger*, *Aspergillus niger* var. *awamori*, *Aspergillus ficuum*, *Aspergillus fumigatus*, *Aspergillus oryzae*, *T. lanuginosus* (also known as *H. lanuginosa*), *Myceliophthora thermophila*, *Peniophora lycii*, *Agrocybe pediades*, *Manascus anka*, *Paxillus involtus*, or *Trametes pubescens*. Suitable fungal phytases are described in Yamada et al., 1986, Agric. Biol. Chem. 322:1275-1282; Piddingtion et al., 1993, Gene 133: 55-62; EP 684,313; EP 0 420 358; EP 0 684 313; WO 98/28408; WO 98/28409; JP 7-67635; WO 98/44125; WO 97/38096; WO 98/13480 in corpporated by reference.

Modified phytases or phytase variants are obtainable by methods known in the art, in particular by the methods disclosed in EP 897,010; EP 897,985; WO 99/49022; WO 99/48330. Commercially available phytases include BIO-FEED PHYTASE™, PHYTASE NOVO™ CT or L (Novozymes A/S, Denmark), or NATUPHOS™ NG 5000 (DSM).

The phytase may preferably be added in the range 5,000-250,000 FYT/g DS, preferably 10,000-100,000 FYT/g DS. A preferred suitable dosage of the phytase is in the range from 0.005-25 FYT/g DS, more preferably 0.01-10 FYT/g, such as 0.1-1 FYT/g DS. Here, the phytase activity is determined using FYT units, one FYT being the amount of enzyme that liberates 1 micromole inorganic ortho-phosphate per min. under the following conditions: pH 5.5; temperature 37° C.; substrate: sodium phytate ($C_6H_6O_{24}P_6Na_2$) at a concentration of 0.0050 mole/l.

Proteases

In another preferred embodiment, the fatty acid oxidizing enzyme treatment is used in combination with at least one protease. The protease may be used, e.g., to digest protein to produce free amino nitrogen (FAN). Such free amino acids function as nutrients for the yeast, thereby enhancing the growth of the yeast and, consequently, the production of ethanol.

The fermenting microorganism for use in a fermentation process may be produced by propagating the fermenting microorganism in the presence of at least one protease. Although not limited to any one theory of operation, it is believed that the propagation of the fermenting microorganism with an effective amount of at least one protease reduces the lag time of the fermenting microorganism when the fermenting microorganism is subsequently used in a fermentation process as compared to a fermenting microorganism that was propagated under the same conditions without the addition of the protease. The action of the protease in the propagation process is believed to directly or indirectly result in the suppression or expression of genes which are detrimental or beneficial, respectively, to the fermenting microorganism during fermentation, thereby decreasing lag time and resulting in a faster fermentation cycle.

Proteases are well known in the art and refer to enzymes that catalyze the cleavage of peptide bonds. Suitable proteases include fungal and bacterial proteases. Preferred proteases are acidic proteases, i.e., proteases characterized by the ability to hydrolyze proteins under acidic conditions below pH 7. Suitable acid fungal proteases include fungal proteases derived from *Aspergillus*, *Mucor*, *Rhizopus*, *Candida*, *Coriolus*, *Endothia*, *Enthomophtra*, *Irpex*, *Penicillium*, *Sclerotium* and *Torulopsis*. Especially contemplated are proteases derived from *Aspergillus niger* (see, e.g., Koaze et al., (1964), *Agr. Biol. Chem. Japan*, 28, 216), *Aspergillus saitoi* (see, e.g., Yoshida, (1954) *J. Agr. Chem. Soc. Japan*, 28, 66), *Aspergillus awamori* (Hayashida et al., (1977) Agric. Biol. Chem., 42(5), 927-933, *Aspergillus aculeatus* (WO 95/02044), or *Aspergillus oryzae*; and acidic proteases from *Mucor pusillus* or *Mucor miehei*.

Bacterial proteases, which are not acidic proteases, include the commercially available products ALCALASE™ and NEUTRASE™ (available from Novozymes A/S). Other proteases include GC106 from Genencor Int, Inc., USA and NOVOZYM™ 50006 from Novozymes A/S, Denmark.

Preferably, the protease is an aspartic acid protease, as described, for example, *Handbook of Proteolytic Enzymes*, Edited by A. J. Barrett, N. D. Rawlings and J. F. Woessner, Academic Press, San Diego, 1998, Chapter 270). Suitable examples of aspartic acid protease include, e.g., those disclosed in R. M. Berka et al. Gene, 96, 313 (1990)); (R. M. Berka et al. *Gene*, 125, 195-198 (1993)); and Gomi et al. *Biosci. Biotech. Biochem.* 57, 1095-1100 (1993), which are hereby incorporated by reference.

Laccase

In another preferred embodiment, the fatty acid oxidizing enzyme treatment is used in combination with laccase. The laccase is applied in an effective amount during fermentation and/or the laccase is applied in an effective amount before or during fermentation, such as, during the propagation of the fermenting microorganisms. Although not limited to any one theory of operation, it is believed that the use of at least one laccase in the fermentation process promotes the oxidation of inhibitors and oxygen depletion, so as to promote the creation of an anaerobic environment more suitable to the fermenting microorganism.

In the context of this invention, laccases and laccase related enzymes comprise any laccase enzyme comprised by the enzyme classification (EC 1.10.3.2), any catechol oxidase enzyme comprised by the enzyme classification (EC 1.10.3.1), any bilirubin oxidase enzyme comprised by the enzyme classification (EC 1.3.3.5) or any monophenol monooxygenase enzyme comprised by the enzyme classification (EC 1.14.18.1).

The above mentioned enzymes may be derived from plants, bacteria or fungi (including filamentous fungi and yeasts) and suitable examples include a laccase derived from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinus*, e.g., *C. cinereus*, *C. comatus*, *C. friesii*, and *C. plicatilis*, *Psathyrella*, e.g., *P. condelleana*, *Panaeolus*, e.g. *P. papilionaceus*, *Myceliophthora*, e.g., *M. thermophila*, *Schytalidium*, e.g., *S. thermophilum*, *Polyporus*, e.g., *P. pinsitus*, *Pycnoporus*, e.g., *P. cinnabarinus*, *Phlebia*, e.g., *P. radita* (WO 92/01046), or *Coriolus*, e.g., *C. hirsutus* (JP 2-238885).

A laccase derived from *Coprinus, Myceliophthora, Polyporus, Pycnoporus, Scytalidium* or *Rhizoctonia* is preferred, in particular a laccase derived from *Coprinus cinereus, Myceliophthora thermophila, Polyporus pinsitus, Pycnoporus cinnabarinus, Scytalidium thermophilum* or *Rhizoctonia solani*.

Amylase

In yet another preferred embodiment, the fatty acid oxidizing enzyme treatment is used in combination with an amylase. Preferred are alpha-amylases of fungal or bacterial origin.

More preferably, the alpha-amylase is a *Bacillus* alpha-amylases, such as, derived from a strain of *B. licheniformis, B. amyloliquefaciens, B. stearothernophilus* and *B. subtilis*. Other alpha-amylases include alpha-amylases derived from a strain of the *Bacillus* sp. NCIB 12289, NCIB 12512, NCIB 12513 or DSM 9375, all of which are described in detail in WO 95/26397, and the alpha-amylase described by Tsukamoto et al., Biochemical and Biophysical Research Communications, 151 (1988), pp. 25-31. Other alpha-amylase variants and hybrids are described in WO 96/23874, WO 97/41213, and WO 99/19467. Other alpha-amylase includes alpha-amylases derived from a strain of *Aspergillus*, such as, *Aspergillus oryzae* and *Aspergillus niger* alpha-amylases. In a preferred embodiment, the alpha-amylase is an acid alpha-amylase. In a more preferred embodiment the acid alpha-amylase is an acid fungal alpha-amylase or an acid bacterial alpha-amylase. More preferably, the acid alpha-amylase is an acid fungal alpha-amylase derived from the genus *Aspergillus*. A commercially available acid fungal amylase is SP288 (available from Novozymes A/S, Denmark).

In a preferred embodiment, the alpha-amylase is an acid alpha-amylase. The term "acid alpha-amylase" means an alpha-amylase (E.C. 3.2.1.1) which added in an effective amount has activity at a pH in the range of 3.0 to 7.0, preferably from 3.5 to 6.0, or more preferably from 4.0-5.0.

A preferred acid fungal alpha-amylase is a Fungamyl-like alpha-amylase. In the present disclosure, the term "Fungamyl-like alpha-amylase" indicates an alpha-amylase which exhibits a high homology, i.e. more than 50%, 55%, 60%, 65%, 70%, 75%, 80%, 85% or even 90% homology to the amino acid sequence shown in SEQ ID No. 10 in WO96/23874. When used as a maltose generating enzyme fungal alpha-amylases may be added in an amount of 0.001-1.0 AFAU/g DS, preferably from 0.002-0.5 AFAU/g DS, preferably 0.02-0.1 AFAU/g DS.

Preferably the alpha-amylase is an acid alpha-amylase, preferably from the genus *Aspergillus*, preferably of the species *Aspergillus niger* or *Aspergillus oryzae*. In a preferred embodiment the acid fungal alpha-amylase is the one from *A. niger* disclosed as "AMYA_ASPNG" in the Swiss-prot/TeEMBL database under the primary accession no. P56271. Also a variant of said acid fungal amylase having at least 70% homology (identity), such as at least 80% homology or even at least 90% homology thereto is contemplated.

Preferred commercial compositions comprising alpha-amylase include MYCOLASE™ from DSM (Gist Brochades), BAN™, TERMAMYL™ SC, FUNGAMYL™, LIQUOZYME™ X and SAN™ SUPER, and SAN™ EXTRA L, (Novozymes A/S) and CLARASE™ L-40,000, DEXLO™, SPEYME FRED, SPEZYME™ AA, and SPEZYME™ DELTA AA (Genencor Int.), and the acid fungal alpha-amylase sold under the trade name SP 288 (available from Novozymes A/S, Denmark).

The amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic alpha-amylase from *B. stearothermophilus* strain NCIB 11837 is commercially available from Novozymes A/S under the tradename NOVAMYL™. Maltogenic alpha-amylases are described in U.S. Pat. Nos. 4,598,048; 4,604,355, and 6,162,628, which are hereby incorporated by reference. Preferably, the maltogenic alpha-amylase is used in a raw starch hydrolysis process, as described, e.g., in WO 95/10627, which is hereby incorporated by reference.

The alpha-amylase may be added in amounts as are well-known in the art. When measured in MU units the acid alpha-amylase activity is preferably present in an amount of 5-50, 0000 AAU/kg of DS, in an amount of 500-50,000 AAU/kg of DS, or more preferably in an amount of 100-10,000 AAU/kg of DS, such as 500-1,000 AAU/kg DS. Fungal acid alpha-amylase are preferably added in an amount of 10-10,000 AFAU/kg of DS, in an amount of 500-2,500 AFAU/kg of DS, or more preferably in an amount of 100-1,000 AFAU/kg of DS, such as approximately 500 AFAU/kg DS.

The glucoamylase used according to an embodiment of the process of the invention may be derived from any suitable source, e.g., derived from a microorganism or a plant. Preferred glucoamylases are of fungal or bacterial origin, selected from the group consisting of *Aspergillus* glucoamylases, in particular *A. niger* G1 or G2 glucoamylase (Boel et al. (1984), EMBO J. 3 (5), p. 1097-1102), or variants thereof, such as disclosed in WO 92/00381 and WO 00/04136; the *A. awamori* glucoamylase (WO 84/02921), *A. oryzae* (Agric. Biol. Chem. (1991), 55 (4), p. 941-949), or variants or fragments thereof.

Other *Aspergillus* glucoamylase variants include variants to enhance the thermal stability: G137A and G139A (Chen et al. (1996), *Prot. Engng.* 9, 499-505); D257E and D293E/Q (Chen et al. (1995), *Prot. Engng.* 8, 575-582); N182 (Chen et al. (1994), *Biochem. J.* 301, 275-281); disulphide bonds, A246C (Fierobe et al. (1996), *Biochemistry*, 35, 8698-8704; and introduction of Pro residues in position A435 and S436 (Li et al. (1997), *Protein Engng.* 10, 1199-1204. Other glucoamylases include *Talaromyces* glucoamylases, in particular, derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). Bacterial glucoamylases contemplated include glucoamylases from the genus *Clostridium*, in particular *C. thermoamylolyticum* (EP 135,138), and *C. thermohydrosulfuricum* (WO 86/01831).

Commercially available compositions comprising glucoamylase include AMG 200L; AMG 300 L; SAN™ SUPER, SAN™ EXTRA L, SPIRIZYME™ PLUS, SPIRIZYME™ FUEL and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR (from Genencor Int.).

Glucoamylases may in an embodiment be added in an amount of 0.02-20 AGU/g DS, preferably 0.1-10 AGU/g DS, such as 2 AGU/g DS.

Xylanase

In another preferred embodiment, the fatty acid oxidizing enzyme treatment is used in combination with a xylanase. The xylanase (E.C. 3.2.1.8) activity may be derived from any suitable source, including fungal and bacterial organisms, such as *Aspergillus, Disporotrichum, Penicillium, Neurospora, Fusarium* and *Trichoderma*.

Preferred commercially available preparations comprising xylanase include SHEARZYME®, BIOFEED WHEAT®, CELLUCLAST®, ULTRAFLO®, VISCOZYME® (Novozymes A/S) and SPEZYME® CP (Genencor Int.).

Cellulase

In yet another preferred, the fatty acid oxidizing enzyme treatment is used in combination with a cellulase. The cellulase activity used according to the invention may be derived from any suitable origin; preferably, the cellulase is of microbial origin, such as derivable from a strain of a filamentous fungus (e.g., *Aspergillus, Trichoderma, Humicola, Fusarium*).

Commercially available preparations comprising cellulase, which may be used include CELLUCLAST™, CELLUZYME™, CEREFLO™ and ULTRAFLO™ (Novozymes A/S), LAMINEX™ and SPEZYME™ CP (Genencor Int.) and ROHAMENT™ 7069 W (from Röhm GmbH).

Production of Enzymes

The fatty acid oxidizing enzyme and other enzymes referenced herein may be derived or obtained from any suitable origin, including, bacterial, fungal, yeast or mammalian origin. The term "derived" or means in this context that the enzyme may have been isolated from an organism where it is present natively, i.e., the identity of the amino acid sequence of the enzyme are identical to a native enzyme. The term "derived" also means that the enzymes may have been produced recombinantly in a host organism, the recombinant produced enzyme having either an identity identical to a native enzyme or having a modified amino acid sequence, e.g., having one or more amino acids which are deleted, inserted and/or substituted, i.e., a recombinantly produced enzyme, which is a mutant and/or a fragment of a. native amino acid sequence or an enzyme produced by nucleic acid shuffling processes known in the art. Within the meaning of a native enzyme are included natural variants. Furthermore, the term "derived" includes enzymes produced synthetically by, e.g., peptide synthesis. The term "derived" also encompasses enzymes which have been modified e.g. by glycosylation, phosphorylation, or by other chemical modification, whether in vivo or in vitro. The term "obtained" in this context means that the enzyme has an amino acid sequence identical to a native enzyme. The term encompasses an enzyme that has been isolated from an organism where it is present natively, or one in which it has been expressed recombinantly in the same type of organism or another, or enzymes produced synthetically by, e.g., peptide synthesis. With respect to recombinantly produced enzymes the terms "obtained" and "derived" refers to the identity of the enzyme and not the identity of the host organism in which it is produced recombinantly.

The enzymes may also be purified. The term "purified" as used herein covers enzymes free from other components from the organism from which it is derived. The term "purified" also covers enzymes free from components from the native organism from which it is obtained. The enzymes may be purified, with only minor amounts of other proteins being present. The expression "other proteins" relate in particular to other enzymes. The term "purified" as used herein also refers to removal of other components, particularly other proteins and most particularly other enzymes present in the cell of origin of the enzyme of the invention. The enzyme may be "substantially pure," that is, free from other components from the organism in which it is produced, that is, for example, a host organism for recombinantly produced enzymes. In preferred embodiment, the enzymes are at least 75% (w/w) pure, more preferably at least 80%, at least 85%, at least 90%, at least 95%, at least 96%, at least 97%, at least 98%, or at least 99% pure. In another preferred embodiment, the enzyme is 100% pure.

The enzymes used according to the present invention may be in any form suitable for use in the processes described herein, such as, e.g., in the form of a dry powder or granulate, a non-dusting granulate, a liquid, a stabilized liquid, or a protected enzyme. Granulates may be produced, e.g., as disclosed in U.S. Pat. Nos. 4,106,991 and 4,661,452, and may optionally be coated by process known in the art. Liquid enzyme preparations may, for instance, be stabilized by adding stabilizers such as a sugar, a sugar alcohol or another polyol, lactic acid or another organic acid according to established process. Protected enzymes may be prepared according to the process disclosed in EP 238,216.

Fermentation Stimulators

In accordance with another preferred embodiment, a fermentation stimulator may be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, e.g., Alfenore et al., Improving ethanol production and viability of *Saccharomyces cerevisia* by a vitamin feeding strategy during fed-batch process," Springer-Verlag (2002), which is hereby incorporated by reference. Examples of minerals include minerals and mineral salts that can supply nutrients comprising P, K, Mg, S, Ca, Fe, Zn, Mn, and Cu.

Liquefaction or Saccharification

Any liquefaction or saccharification may be used in combination with the fermentation process of the present invention. According to the present invention the saccharification and liquefaction may be carried out simultaneously or separately with the fermentation process. In a preferred embodiment of the present invention, the liquefaction, saccharification and fermentation processes are carried out simultaneously (LSF).

"Liquefaction" is a process in which milled (whole) grain raw material is broken down (hydrolyzed) into maltodextrins (dextrins). Liquefaction is often carried out as a three-step hot slurry process. The slurry is heated to between 60-95° C., preferably 80-85° C., and the enzymes are added to initiate liquefaction (thinning). The slurry is then jet-cooked at a temperature between 95-140° C., preferably 105-125° C. to complete gelanitization of the slurry. Then the slurry is cooled to 60-95° C. and more enzyme(s) is(are) added to finalize hydrolysis (secondary liquefaction). The liquefaction process is usually carried out at pH 4.5-6.5, in particular at a pH between 5 and 6. Milled and liquefied whole grains are known as mash.

The liquefaction processes are typically carried out using any of the alpha-amylase listed above in the "Amylase" section.

"Saccharification" is a process in which the maltodextrin (such as, produced from the liquefaction process) is converted to low molecular sugars $DP_{1-3}$ (i.e., carbohydrate source) that can be metabolized by the fermenting organism, such as, yeast. Saccharification processes are well known in the art and are typically performed enzymatically using a glucoamylase. Alternatively or in addition, alpha-glucosidases or acid alpha-amylases may be used. A full saccharification process may last up to from about 24 to about 72 hours, and is often carried out at temperatures from about 30 to 65° C., and a pH between 4 and 5, normally at about pH 4.5. However, it is often more preferred to do a pre-saccharification step, lasting for about 40 to 90 minutes, at temperature of between 30-65° C., typically about 60° C., followed by complete saccharification during fermentation in a simultaneous saccharification and fermentation process (SSF).

The most widely used process in ethanol production is the simultaneous saccharification and fermentation (SSF) process, in which there is no holding stage for the saccharification, meaning that fermenting organism, such as the yeast, and enzyme(s) is(are) added together. In SSF processes, it is common to introduce a pre-saccharification step at a temperature above 50° C., just prior to the fermentation.

More preferably, the liquefaction, saccharification or fermentation process is a simultaneous liquefaction-saccharification-fermentation (LSF) process or single enzymatic process, in which the liquefaction, saccharification and fermentation process are all carried out in one process, that is, all enzymes (or substitutable or additional non-enzymatic agents) used for liquefaction, saccharification and fermentation are added in the same process step, more preferably, simultaneously in the same process step. Preferred process conditions for LSF process include temperatures of about 26° C. to 40° C., preferably about 32° C., pH of about 4 to about 8, preferably about pH 5, and process times of about 48 to 72 hours, preferably about 72 hours.

Preferably, the LSF process or single enzymatic process is a raw starch hydrolysis (RSH) processes, more preferably, used in the production of alcohol, such as, e.g., ethanol. A "raw starch hydrolysis" process (RSH) differs from conventional starch treatment processes in that raw uncooked starch, also referred to as granular starch, is used in the ethanol fermentation process. As used herein, the term "granular starch" means raw uncooked starch, i.e., starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called gelatinization begins.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch is the temperature at which birefringence is lost in 5% of the starch granules using the process described by Gorinstein. S. and Lii. C., Starch/Stärke, Vol. 44 (12) pp. 461-466 (1992).

In accordance with a preferred embodiment, fatty acid oxidizing enzyme can be used, preferably in combination with esterases, a phytase, laccase, protease, amylases and/or a glucoamylases, to increase ethanol yield in raw starch hydrolysis processes.

In a preferred embodiment, the present invention involves treating granular starch slurry with a fatty acid oxidizing enzyme and one or more of activity from the group of phytase, esterase, protease, laccase, glucoamylase and/or (maltogenic) alpha-amylase, yeast at a temperature below the initial gelatinizatiion temperature of granular starch. Preferably, the yeast is Ethanol Red yeast. The amylase is preferably an acid alpha-amylase, more preferably an acid fungal alpha-amylase.

In a more preferred embodiment, the raw starch hydrolysis process entails, treating granular starch slurry with a glucoamylase and/or alpha-amylase at a temperature between 0° C. and 20° C. below the initial gelatinization temperature of the granular starch, followed by treating the slurry with a glucoamylase and/or alpha amylase, yeast and at least one fatty acid oxidazing enzyme, and optionally an esterase, protease, phytase, laccase, amylase and/or glucoamylase at a temperature of between 10° C. and 35° C.

In yet another preferred embodiment, the process entails the sequential steps of: (a) treating a granular starch slurry with an acid alpha-amylase and a glucoamylase at a temperature of 0° C. to 20° C. below the initial gelatinization temperature of the granular starch, preferably for a period of 5 minutes to 12 hours, (b) treating the slurry in the presence of an acid alphaamylase, a glucoamylase, a yeast and at least one fatty acid oxidizing enzyme, and optionally a phytase, protease, laccase, esterase at a temperature of between 10° C. and 35° C., preferably for a period of 20 to 250 hours to produce ethanol.

Other enzymes and fermentation stimulators may be used in combination with the fatty acid oxidizing enzyme treatment in the RSH process. Preferably, the other enzyme is selected from the group consisting of an esterase, such as lipase, or cutinase, phytase, protease, cellulase, xylanase, and alpha-amylase, such as a maltogenic alpha-amylase, glucoamylase and combinations thereof. In RSH processes, phytic acid is present in significant amounts. Accordingly, in a preferred embodiment, phytases can be used to promote the liberation of inorganic phosphate from phytic acid (myo-inositol hexakisphosphate) or from any salt thereof (phytates), as previously described.

In another preferred embodiment, a maltogenic alpha-amylase is used in combination with the fatty acid oxidizing enzyme treatment in the RSH process.

A preferred application of the fermentation processes and compositions described herein is in an alcohol production process (such as, e.g., ethanol for use as a fuel or fuel additive), more preferably using a raw starch hydrolysis process. The processes described herein can be used, e.g., to increase the rate and/or yield of ethanol production. The addition of an effective amount of at least one fatty acid oxidizing enzyme can be used to improve ethanol yield of the fermentation product.

Ethanol production processes generally involve the steps of milling, liquefaction, saccharification, fermentation and distillation. In the production of ethanol and other starch-based products, the raw material, such as whole grain, preferably corn, is milled in order to open up the structure and allow for further processing. Two processes are preferred according to the invention: wet milling and dry milling. Preferred for ethanol production is dry milling where the whole kernel is milled and used in the remaining part of the process. Wet milling may also be used and gives a good separation of germ and meal (starch granules and protein) and is with a few exceptions applied at locations where there is a parallel production of syrups. Both wet and dry milling processes are well known in the art.

In ethanol production, the fermenting organism is preferably yeast, which is applied to the mash. Preferred yeast is derived from *Saccharomyces* spp., more preferably, from *Saccharomyces cerevisiae*. In preferred embodiments, yeast is applied to the mash and the fermentation is ongoing for 24-96 hours, such as typically 35-60 hours. In preferred embodiments, the temperature is generally between 26-34° C., in particular about 32° C., and the pH is generally from pH 3-6, preferably around pH 4-5. Yeast cells are preferably applied in amounts of $10^5$ to $10^{12}$, preferably from $10^7$ to $10^{10}$, especially $5 \times 10^7$ viable yeast count per ml of fermentation broth. During the ethanol producing phase the yeast cell count should preferably be in the range from $10^7$ to $10^{10}$, especially around $2 \times 10^8$. Further guidance in respect of using yeast for fermentation can be found in, e.g., "The alcohol Textbook" (Editors K. Jacques, T. P. Lyons and D. R. Kelsall, Nottingham University Press, United Kingdom 1999), which is hereby incorporated by reference.

Following fermentation, the mash may be distilled to extract the alcohol product (ethanol). In the case where the end product is ethanol, obtained according to the processes of the invention, it may be used as, e.g., fuel ethanol; drinking ethanol, i.e., potable neutral spirits; or industrial ethanol.

In an aspect the invention relates to a process for producing ethanol, comprising
(a) milling whole grains;
(b) liquefying the product of step (a);
(c) saccharifying the liquefied material;
(d) fermenting the saccharified material using a microorganism, wherein the fermentation process further comprises contacting the fermentation media with at least one fatty acid oxidizing enzyme.

The fatty acid oxidizing enzyme and additional enzymes and stimulators may be any of the above mentioned. The preferred fatty acid oxidizing enzyme is lipoxygenase.

In a final aspect the invention relates to a composition comprising a fatty acid oxidizing enzyme and one or more enzymes selected from the group consisting of an esterase, phytase, laccase, protease, cellulase, xylanase, amylase, such as alpha-amylase or glycoamylase, or mixtures thereof. In a preferred embodiment the fatty acid oxidizing enzymes is a lipoxygenase (LOX), preferably any of the one mentioned above. In an embodiment the composition further comprises a lipase, and optionally an alpha-amylase and/or glucoamylase.

MATERIALS AND METHODS

Fatty acid oxidizing enzyme: Lipoxygenase derived from *Magnaporthe salvinii*, disclosed in WO 02/086114 (available from Novozymes A/S, Denmark).
Lipase: LIPOLASE™ 100 L (availablke from Novozymes A/S, Denmark)
Glucoamylase: SPIRIZYME FUEL (available from Novozymes A/S)
Protease: NOVOZYM™ 50006 available from Novozymes A/S, Denmark)
Yeast: Ethanol Red available from Red Star/Lesaffre, USA Methods:

Preparation of Backset:
Centrate after centrifugation of fermented raw starch from a beer stripper column Lipoxygenase Activity Lipoxygenase activity may be determined spectrophotometrically at 25° C. by monitoring the formation of hydroperoxides. For the standard analysis, 10 micro liters enzyme is added to a 1 ml quartz cuvette containing 980 micro liter 25 mM sodium phosphate buffer (pH 7.0) and 10 micro liter of substrate solution (10 mM linoleic acid dispersed with 0.2% (v/v) Tween20 (should not be kept for extended time periods)). The enzyme is typically diluted sufficiently to ensure a turn-over of maximally 10% of the added substrate within the first minute. The absorbance at 234 nm is followed and the rate is estimated from the linear part of the curve. The cis-trans-conjugated hydro(pero)xy fatty acids are assumed to have a molecular extinction coefficient of 23,000 $M^-cm^{-1}$.

Alpha-Amylase Activity (KNU)

The amylolytic activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e. at 37° C. +/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Phytase Activity

The phytase activity is measured in FYT units, one FYT being the amount of enzyme that liberates 1 micromole inorganic ortho-phosphate per min. under the following conditions: pH 5.5; temperature 37° C.; substrate: sodium phytate ($C_6H_6O_{24}P_6Na_{12}$) at a concentration of 0.005 mole/l.

Determnination of FAU Activity

One Fungal Alpha-Amylase Unit (FAU) is defined as the amount of enzyme, which breaks down 5.26 g starch (Merck Amylum solubile Erg. B.6, Batch 9947275) per hour based upon the following standard conditions:

| | |
|---|---|
| Substrate | Soluble starch |
| Temperature | 37° C. |
| pH | 4.7 |
| Reaction time | 7-20 minutes |

Reaction time . . . 7-20 minutes

Determination of Acid Alpha-Amylase Activity (AFAU)

Acid alpha-amylase activity is measured in AFAU (Acid Fungal Alpha-amylase Units), which are determined relative to an enzyme standard.

The standard used is AMG 300 L (from Novozymes A/S, Denmark, glucoamylase wild-type *Aspergillus niger* G1, also disclosed in Boel et al. (1984), EMBO J. 3 (5), p. 1097-1102) and WO 92/00381). The neutral alpha-amylase in this AMG falls after storage at room temperature for 3 weeks from approx. 1 FAU/mL to below 0.05 FAU/mL.

The acid alpha-amylase activity in this AMG standard is determined in accordance with the following description. In this method, 1 AFAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

| Starch + Iodine | Alpha-amylase → 40° C., pH 2.5 | Dextrins + Oligosaccharides |
|---|---|---|
| Blue/violet | t = 23 sec. | Decoloration |

| Standard conditions/reaction conditions: (per minute) | |
|---|---|
| Substrate: | Starch, approx. 0.17 g/L |
| Buffer: | Citate, approx. 0.03 M |
| Iodine (I$_2$): | 0.03 g/L |
| CaCl$_2$: | 1.85 mM |
| pH: | 2.50 ± 0.05 |
| Incubation temperature: | 40° C. |
| Reaction time: | 23 seconds |
| Wavelength: | lambda = 590 nm |
| Enzyme concentration: | 0.025 AFAU/mL |
| Enzyme working range: | 0.01-0.04 AFAU/mL |

If further details are preferred these can be found in EB-SM-0259.02/01 available on request from Novozymes A/S, Denmark, and incorporated by reference.

Acid Alpha-Amylase Units (AAU)

The acid alpha-amylase activity can be measured in AAU (Acid Alpha-amylase Units), which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

| Standard conditions/reaction conditions: | |
|---|---|
| Substrate: | Soluble starch. Concentration approx. 20 g DS/L. |
| Buffer: | Citrate, approx. 0.13 M, pH = 4.2 |
| Iodine solution: | 40.176 g potassium iodide + 0.088 g iodine/L |
| City water: | 15°-20° dH (German degree hardness) |
| pH: | 4.2 |
| Incubation temperature: | 30° C. |
| Reaction time: | 11 minutes |
| Wavelength: | 620 nm |
| Enzyme concentration: | 0.13-0.19 AAU/mL |
| Enzyme working range: | 0.13-0.19 AAU/mL |

The starch should be Lintner starch, which is a calorimetric indicator. Lintner starch is obtained by dilute hydrochloric acid treatment of native starch so that it retains the ability to color blue with iodine. Further details can be found in EP0140410B2, which disclosure is hereby included by reference.

Determination of Glucoamylase Activity (AGI)

Glucoamylase (equivalent to amyloglucosidase) converts starch into glucose. The amount of glucose is determined here by the glucose oxidase method for the activity determination. The method described in the section 76-11 Starch-Glucoamylase Method with Subsequent Measurement of Glucose with Glucose Oxidase in "Approved methods of the American Association of Cereal Chemists". Vol. 1-2 AACC, from American Association of Cereal Chemists, (2000); ISBN: 1-891127-12-8.

One glucoamylase unit (AGI) is the quantity of enzyme which will form 1 micromol of glucose per minute under the standard conditions of the method.

| Standard conditions/reaction conditions: | |
|---|---|
| Substrate: | Soluble starch. Concentration approx. 16 g dry matter/L. |
| Buffer: | Acetate, approx. 0.04 M, pH = 4.3 |
| pH: | 4.3 |
| Incubation temperature: | 60° C. |
| Reaction time: | 15 minutes |
| Termination of the reaction: | NaOH to a concentration of approximately 0.2 g/L (pH~9) |
| Enzyme concentration: | 0.15-0.55 AAU/mL. |

The starch should be Lintner starch, which is a thin-boiling starch used in the laboratory as colorimetric indicator. Lintner starch is obtained by dilute hydrochloric acid treatment of native starch so that it retains the ability to color blue with iodine.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1 M |
| pH: | 4.30 ± 0.05 |
| Incubation temperature: | 37° C. ± 1 |
| Reaction time: | 5 minutes |
| Enzyme working range: | 0.5–4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12 M; 0.15 M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Determination of Cutinase Activity (LU)

The cutinase activity is determined as lipolytic activity determined using tributyrine as substrate. This method was based on the hydrolysis of tributyrin by the enzyme, and the alkali consumption is registered as a function of time. One Lipase Unit (LU) is defined as the amount of enzyme which, under standard conditions (i.e. at 30.0 degree celsius; pH 7.0; with Gum Arabic as emulsifier and tributyrine as substrate)

liberates 1 micro mol titrable butyric acid per minute. A folder AF 95/5 describing this analytical method in more detail is available upon request from Novozymes A/S, Denmark, which folder is hereby included by reference.

Xylanolytic Activity (FXU)

The xylanolytic activity can be expressed in FXU-units, determined at pH 6.0 with remazol-xylan (4-O-methyl-D-glucurono-D-xylan dyed with Remazol Brilliant Blue R, Fluka) as substrate.

A xylanase sample is incubated with the remazol-xylan substrate. The background of non-degraded dyed substrate is precipitated by ethanol. The remaining blue color in the supernatant (as determined spectrophotometrically at 585 nm) is proportional to the xylanase activity, and the xylanase units are then determined relatively to an enzyme standard at standard reaction conditions, i.e. at 50.0° C., pH 6.0, and 30 minutes reaction time.

A folder EB-SM-352.02/01 describing this analytical method in more detail is available upon request to Novozymes A/S, Denmark, which folder is hereby included by reference.

Determination of Maltogenic Amylase Activity (MANU)

One MANU (Maltogenic Amylase Novo Unit) may be defined as the amount of enzyme required to release one micro mole of maltose per minute at a concentration of 10 mg of maltotriose (Sigma M 8378) substrate per ml of 0.1 M citrate buffer, pH 5.0 at 37 □C for 30 minutes.

Cellulytic Activity (EGU)

The cellulytic activity may be measured in endo-glucanase units (EGU), determined at pH 6.0 with carboxymethyl cellulose (CMC) as substrate. A substrate solution is prepared, containing 34.0 g/l CMC (Hercules 7 LFD) in 0.1 M phosphate buffer at pH 6.0. The enzyme sample to be analyzed is dissolved in the same buffer. 5 ml substrate solution and 0.15 ml enzyme solution are mixed and transferred to a vibration viscosimeter (e.g. MIVI 3000 from Sofraser, France), thermostated at 40° C. for 30 minutes. One EGU is defined as the amount of enzyme that reduces the viscosity to one half under these conditions. The amount of enzyme sample should be adjusted to provide 0.01-0.02 EGU/ml in the reaction mixture. The arch standard is defined as 880 EGU/g.

A folder EB-SM-0275.02/01 describing this analytical method in more detail is available upon request to Novozymes A/S, Denmark, which folder is hereby included by reference.

EXAMPLES

Example 1

Measurement of the Activity of Fatty Acid Oxidizing Enzymes on Linoleic Acid

An "Oxi 3000 Oximeter" (WTW, Weilheim, Germany) with a TriOxmatic 300 oxygen electrode and a standard reaction volume of 4 ml was used.

10 mg linoleic acid (10 ml 60% linoleic acid) was dissolved in 1 ml ethanol, and 2 micro liter Tween 20 was added. From this stock substrate solution 50 micro liter was added into a reaction beaker containing 3.85 ml buffer solution (Britton-Robinson: 100 mM of Phosphoric-, Acetic- and Boric acid; pH adjusted with NaOH) with a small stir bar allowing the solution to be mixed well, and the oxygen electrode was inserted into the reaction beaker. 100 micro liter purified enzyme solution was added, viz. (a) lipoxygenase derived from *Magnaporthe salvinii* at a concentration of approx. 0.4 mg/ml; or (b) lipoxygenase derived from *Gaeumannomyces. graminis* at a concentration of approx. 0.76 mg/ml (which means approximately 0.02 mg/ml in the final reaction). These lipoxygenases were prepared as previously described. The temperature was 25° C. The concentration of dissolved oxygen (mg/l) is measured and plotted as a function of time (min.). The enzymatic activity is calculated as the slope of the linear part of the curve (mg/l/min.) after addition of the enzyme. The baseline was corrected by subtraction when relevant, meaning that if the curve showing oxygen concentration as a function of time had a slope of above about 0.05 mg oxygen/ml/min before addition of the fatty acid oxidizing enzyme (i.e. the control), this value was subtracted from the sample slope value.

Table 1 below shows the results of the experiments.

TABLE 1

| | Fatty Acid Oxidizing Enzyme | |
| --- | --- | --- |
| pH | (a) LOX from *M. salvinii* mgO$_2$/ml/min | (b) LOX from *G. graminis* mgO$_2$/ml/min |
| 2 | 0.0 | 0.0 |
| 4 | 0.4 | 0.1 |
| 5 | 0.7 | 0.4 |
| 6 | 1.1 | 0.4 |
| 7 | 1.0 | 0.4 |
| 8 | 0.7 | 0.5 |
| 9 | 0.8 | 0.4 |
| 10 | 0.7 | 0.4 |
| 11 | 0.6 | 0.2 |

Example 2

Fatty Acid Oxidizing Enzymes

Four enzymes, viz. two laccases and two lipoxygenases were tested as described below. The laccase derived from *Polyporus pinsitus* had a MW by SDS-Page of 65 kDa, a pi by IEF of 3.5, and an optimum temperature at pH 5.5 of 60° C. The laccase derived from *Coprinus cinereus* had a MW by SDS-Page of 67-68 kDa, a pI by IEF of 3.5-3.8, and an optimum temperature at pH 7.5 of 65° C. The enzymes were prepared and purified as described in WO 96/00290 and U.S. Pat. No. 6,008,029. The two lipoxygenases were derived from *Magnaporthe salvinii* and *Gaeumannomyces graminis*, and they were prepared as described previously.

The enzyme dosage was adjusted to ensure maximum absorbancy increase per minute at 234 nm /530 nm, viz. in the range of 0.1-0.25 absorbancy units pr. min.

Substrate solution: 11.65 mg linoleic acid (60% Sigma), as well as 12.5 ml 0.56 mM Syringaldazine (Sigma) in ethanol was mixed with deionized water to a total volume of 25 ml.

50 microliter of the enzyme preparation to be tested was transferred to a quartz cuvette containing 900 microliter phosphate buffer (50 mM, pH 7.0) and 50 microliter of the substrate solution The cuvette was placed in a spectrofotometer, thermostated at 23° C., and the absorbancies at 234 nm and 530 nm were measured as a function of time. The absorbancy at 530 nm is indicative of degradation of syringaldazine, whereas the absorbancy at 234 nm is indicative of degradation of linoleic acid. The absorbancy increase as a function of time is calculated on the basis of minutes 2 to 4 of the reaction time, i.e. d($A_{234}$)/dt, as well as d($A_{530}$)/dt.

The results are shown in Table 2 below. Of these four enzymes, only the two lipoxygenases qualify as a fatty acid oxidizing enzyme as defined herein. This is because RRD=Reaction Rate Difference=$(dA_{234}/dt - dA_{530}/dt)$ is above zero only for these two enzymes.

TABLE 2

| Enzyme | $dA_{530}/dt$ (units/min) | $dA_{234}/dt$ (units/min) | $dA_{234}/dt - dA_{530}/dt$ (units/min) |
|---|---|---|---|
| *Polyporus pinsitus* laccase | 0.20 | 0.002* | −0.20 |
| *Magnaporthe salvinii* lipoxygenase | 0.0001* | 0.13 | 0.13 |
| *Coprinus cinereus* laccase | 0.17 | −0.001* | −0.17 |
| *Gaeumannomyces graminis* lipoxygenase | −0.03* | 0.21 | 0.21 |

*this is equivalent to zero activity (analytical inaccuracy)

Example 3

LSF Including 50% w/w Backset

Raw starch hydrolysis (RSH) was carried out as follows: Ethanol Red yeast was propagated aerobically at 500 rpm and 32.2° C. for 8 hours in the presence of 0.02% DS NOVOZYM 50006™. A corn slurry (36% DS) was prepared by mixing ground corn (2-mm screen), tap water and backset followed by pH adjustment to pH 5 with phosphoric acid. The content of backset was 50% w/w of the liquid phase. SP288, 0.8 AFAU/g DS, SPIRIZYME™ FUEL, 2 AGU/g DS, and yeast propagate was introduced into the slurry immediately before filling 25-ml fermenters equipped with the air locks. The air locks were provided with 0.2-micro m syringe filters to prevent oil backflow and microbial contaminations. The fermentation was carried out at 32.2° C. for 64 hours. When fermentation was completed fermenters were spin down at 3,000 rpm at 20° C. for 15 minutes. The supernatant was forced through a 0.45-micro m filter and analyzed by HPLC.

TABLE 1

| Backset, % | Ethanol, % v/v |
|---|---|
| Control | 19.81 |
| 50 | 17.77 |

Effect of backset concentration on 64-hours ethanol yield in RSH. Data are average of 7 fermentations done at different time. Table 1 shows that the addition of backset to the fermentation medium decreases the ethanol yield.

Example 4

LSF with *Magnaporthe Salvinii* lipoxygenase Pretreated Fermentation Medium and 50% Backset The experiment described in Example 3 was repeated using a fermentation medium pretreated with lipoxygenase and lipoxygenase with lipase incorporated in the fermentation medium.

TABLE 2

| Lipoxygenase activity, U/g DS | Lipase | Activity, LU/g DS | Ethanol, % v/v in beer |
|---|---|---|---|
| 0 | — | — | 17.77 |
| 9.3 | — | — | 18.76 |
| 9.3 | LIPOLASE ™100 L | 5 | 19.13 |

Table 2 shows that 1) lipoxygenase and 2) lipoxygenase and lipase pretreatment of the fermentation medium increases the ethanol yields.

The invention claimed is:

1. A process for producing ethanol in a fermentation medium which process comprises a fermentation step with a microorganism, comprising subjecting the fermentation medium to at least one fatty acid oxidizing enzyme.

2. The process of claim 1, wherein the fatty acid oxidizing enzyme is a lipoxygenase.

3. The process of claim 2, wherein the lipoxygenase is derived from *Fusarium oxysporum, Fusarium proliferatum, Gaeumannomyces graminis*, a strain of *Geotrichum, Magnaporthe salvinii, Pyricularia oryzae, Saccharomyces cerevisiae, Thermoactinomyces vulgaris*, or *Thermomyces lanuginosus*.

4. The process of claim 1, wherein the microorganism is yeast.

5. The process of claim 1, wherein the fermentation step is part of a simultaneous saccharification and fermentation process or a liquefaction, saccharification, and fermentation process.

6. The process of claim 1, wherein the fermentation is carried out in the presence of one or more enzymes selected from the group consisting of an esterase, phytase, cellulase, xylanase, laccase, protease, alpha-amylase, and glucoamylase.

7. The process of claim 1, wherein the fermentation is part of a dry milling process or of a wet milling process.

8. The process of claim 7, wherein the raw material for milling process is a starch-containing raw material.

9. A process for producing ethanol, comprising
   (a) milling whole grains;
   (b) liquefying the product of step (a);
   (c) saccharifying the liquefied material; and
   (d) fermenting the saccharified material using a microorganism, wherein the fermentation process further comprises contacting the fermentation media with at least one fatty acid oxidizing enzyme.

10. The process of claim 9, further comprising distilling the fermented material.

11. The process of claim 9, wherein the process is a simultaneous liquefaction and saccharification process or a simultaneous liquefaction, saccharification and fermentation process.

12. The process of claim 9, wherein the process comprises adding one or more enzymes selected from the group consisting of esterases.

13. The process of claim 9, wherein the fatty acid oxidizing enzyme is a lipoxygenase.

14. The process of claim 9, wherein the microorganism is yeast.

* * * * *

UNITED STATES PATENT AND TRADEMARK OFFICE
CERTIFICATE OF CORRECTION

PATENT NO.        : 7,582,458 B2
APPLICATION NO. : 11/299163
DATED             : September 1, 2009
INVENTOR(S)       : Varvara Grichko It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 566 days.

Signed and Sealed this

Fourteenth Day of September, 2010

David J. Kappos
*Director of the United States Patent and Trademark Office*